US009726686B2

(12) United States Patent
Mellars et al.

(10) Patent No.: US 9,726,686 B2
(45) Date of Patent: Aug. 8, 2017

(54) ENCODING SCHEME EMBEDDED INTO AN AUTOMATION TRACK SURFACE

(71) Applicants: Colin Mellars, Dover, NJ (US); Baris Yagci, Whippany, NJ (US); Benjamin Pollack, Budd Lake, NJ (US)

(72) Inventors: Colin Mellars, Dover, NJ (US); Baris Yagci, Whippany, NJ (US); Benjamin Pollack, Budd Lake, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/376,111

(22) PCT Filed: Feb. 1, 2013

(86) PCT No.: PCT/US2013/024353
§ 371 (c)(1),
(2) Date: Jul. 31, 2014

(87) PCT Pub. No.: WO2013/116654
PCT Pub. Date: Aug. 8, 2013

(65) Prior Publication Data
US 2015/0010437 A1 Jan. 8, 2015

Related U.S. Application Data

(60) Provisional application No. 61/594,486, filed on Feb. 3, 2012.

(51) Int. Cl.
*G01N 35/04* (2006.01)
*G01N 35/00* (2006.01)
*G01N 35/02* (2006.01)

(52) U.S. Cl.
CPC . *G01N 35/00732* (2013.01); *G01N 35/00722* (2013.01); *G01N 35/02* (2013.01);
(Continued)

(58) Field of Classification Search
CPC ......... B65G 47/493; G01N 2035/0491; G05D 1/0234; B62D 1/283
See application file for complete search history.

(56) References Cited

U.S. PATENT DOCUMENTS 3,749,916 A 7/1973 Thomas et al.
4,566,032 A * 1/1986 Hirooka .................. B66F 9/063
180/168
(Continued)

FOREIGN PATENT DOCUMENTS

JP S61-055705 U 4/1986
JP S61-082937 U 6/1986
(Continued)

OTHER PUBLICATIONS

PCT International Search Report and Written Opinion dated Apr. 11, 2013 (8 Pages).
(Continued)

*Primary Examiner* — P. Kathryn Wright

(57) ABSTRACT

An automation system for an in vitro diagnostics environment includes a plurality of intelligent carriers that include onboard processing and navigation capabilities. A central scheduler can communicate wirelessly with the carriers to direct the carriers to carry a fluid sample to testing stations along a track within the automation system. The carriers can utilize landmarks and distance encoding to reach destinations accurately and quickly, including, for example within less than the time for a single operation cycle of an automated clinical analyzer. The distance encoding can include optical marks repeated at regular intervals (pitch), where the intervals are conveyed to the carriers wirelessly or via optical encoding. The pitch of the encoding can differ for different sections of track depending on the position precision desired.

22 Claims, 14 Drawing Sheets

(52) U.S. Cl.
CPC ... *G01N 35/04* (2013.01); *G01N 2035/00772* (2013.01); *G01N 2035/00801* (2013.01); *G01N 2035/00851* (2013.01); *G01N 2035/0406* (2013.01)

(56) References Cited

U.S. PATENT DOCUMENTS

| | | | |
|---|---|---|---|
| 4,777,601 A * | 10/1988 | Boegli | G05D 1/0234 180/168 |
| 5,814,961 A * | 9/1998 | Imahashi | G05D 1/0234 180/168 |
| 6,202,829 B1 | 3/2001 | Van Dyke, Jr. et al. | |
| 2002/0102910 A1* | 8/2002 | Donahue | A63H 18/16 446/465 |
| 2003/0044319 A1 | 3/2003 | Itoh | |
| 2003/0220761 A1 | 11/2003 | Biwa | |
| 2005/0171656 A1* | 8/2005 | Hori | B65G 1/0421 701/19 |
| 2007/0016341 A1* | 1/2007 | Nagasawa | B60T 7/18 701/1 |
| 2007/0225857 A1 | 9/2007 | Barry et al. | |
| 2009/0084657 A1 | 4/2009 | Brandt et al. | |
| 2009/0173040 A1 | 7/2009 | Carlson et al. | |

FOREIGN PATENT DOCUMENTS

| | | |
|---|---|---|
| JP | S61-213905 A | 9/1986 |
| JP | H06-012123 A | 1/1994 |
| JP | H11-500224 A | 1/1999 |
| JP | H11-242039 A | 7/1999 |
| JP | H11-264828 A | 9/1999 |
| JP | 2001174468 A | 6/2001 |
| JP | 2001-278409 A | 10/2001 |
| JP | 2003-076423 A | 3/2003 |
| JP | 2005-030855 A | 2/2005 |
| JP | 2005-202464 A | 7/2005 |
| JP | 2005-300220 A | 10/2005 |
| JP | 2007-025744 A | 2/2007 |
| JP | 2008-058202 A | 3/2008 |
| JP | 2010-526289 A | 7/2010 |
| WO | 2011/138448 A1 | 11/2011 |
| WO | 2012/158541 A1 | 11/2012 |

OTHER PUBLICATIONS

Extended EP Search Report dated Sep. 30, 2015 of corresponding European Patent Application No. 13743503.8, 4 Pages.

\* cited by examiner

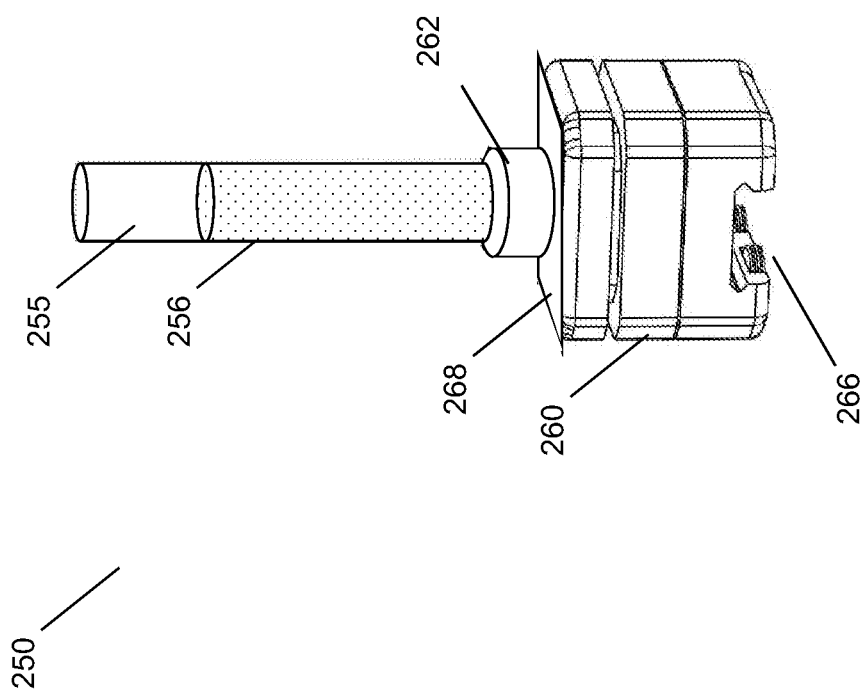

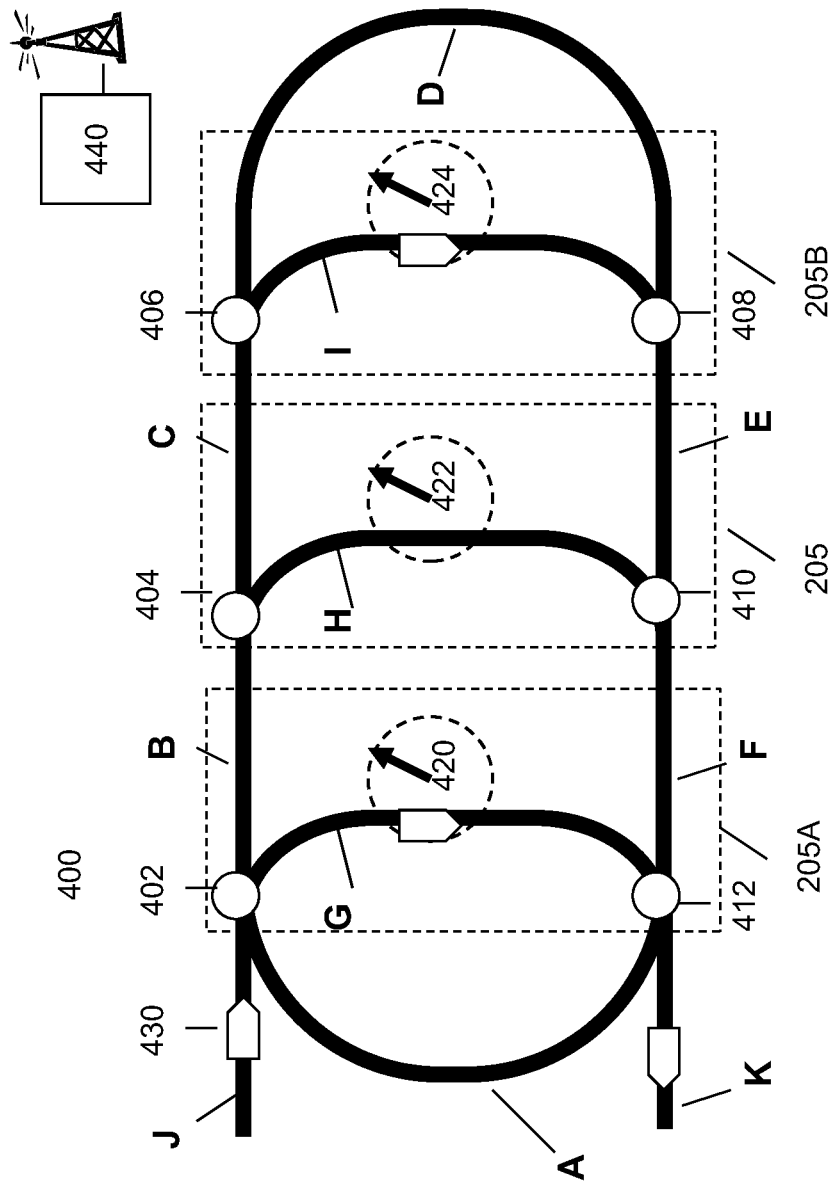

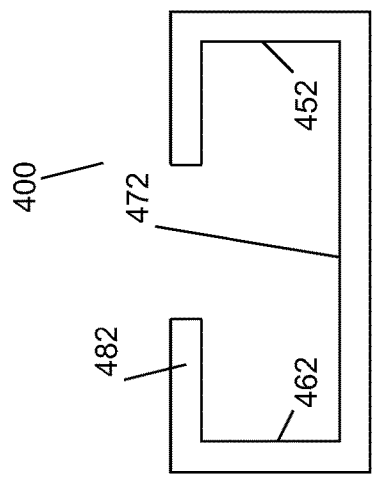
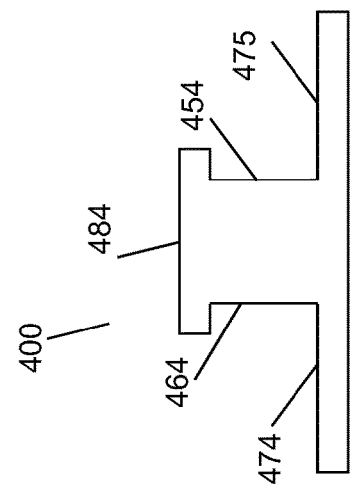
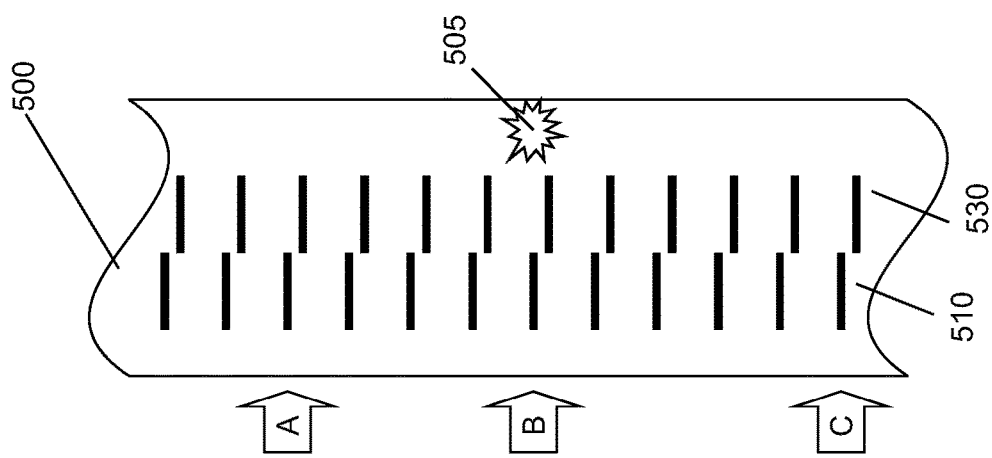
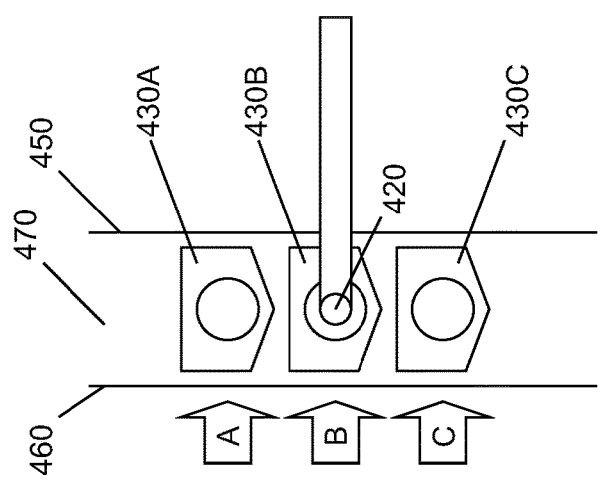

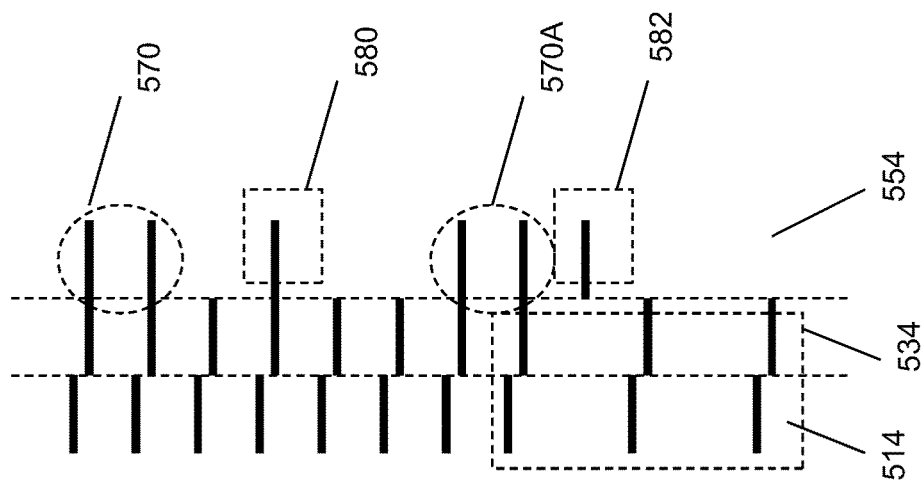

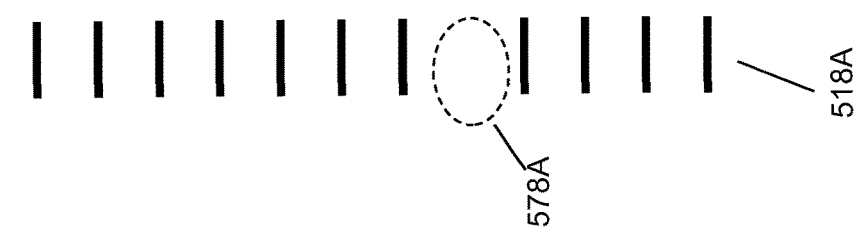
FIG. 9D
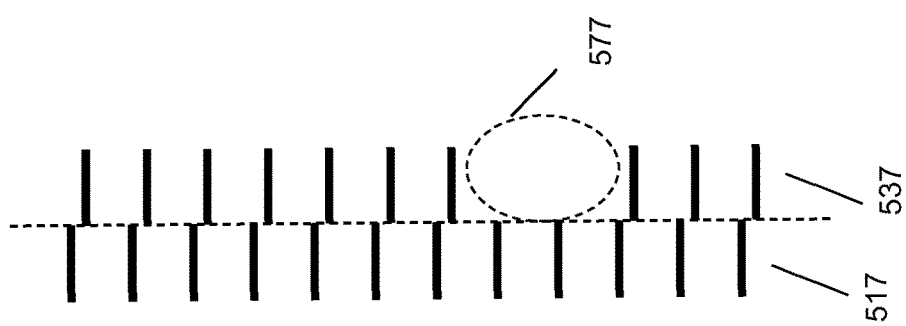
FIG. 9C
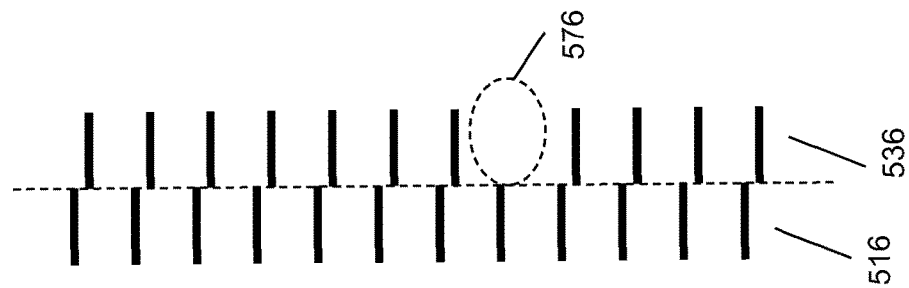
FIG. 9B
FIG. 9A

ENCODING SCHEME EMBEDDED INTO AN AUTOMATION TRACK SURFACE

CROSS-REFERENCE TO RELATED APPLICATIONS

This application claims priority to U.S. provisional application Ser. No. 61/594,486 filed Feb. 3, 2012, which is incorporated herein by reference in its entirety.

TECHNOLOGY FIELD

The present invention relates in general to an automation system for use in a laboratory environment and, more particularly to systems and methods for transporting patient samples for in vitro diagnostics in a clinical analyzer via active transport devices. Embodiments of the present invention are particularly well suited, but in no way limited, to optical encoding for conveying local position information to independent carriers having active direction and routing capabilities.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer, which may include immunoassay (IA) and clinical chemistry (CC) stations. Some traditional IVD automation track systems comprise systems that are designed to transport samples from one fully independent module to another standalone module. This allows different types of tests to be specialized in two different stations or allows two redundant stations to be linked to increase the volume of sample throughput available. These lab automation systems, however, are often bottlenecks in multi-station analyzers. Relatively speaking, traditional lab automation systems lack large degrees of intelligence or autonomy to allow samples to independently move between stations.

In an exemplary prior art system, a friction track, much like a conveyor belt, shuttles individual carrier mechanisms, sometimes called pucks, or racks of containers between different stations. Samples may be stored in sample containers, such as test tubes that are placed into a puck by an operator or robot arm for transport between stations in an analyzer along the track. This friction track, however, can only move in one direction at a time and any samples on the track will move in the same direction at the same speed. When a sample needs to exit the friction track, gating/switching can be used to move individual pucks into offshoot paths. A drawback with this set up is that singulation must be used to control the direction of any given puck at each gate and switch. For example, if two pucks are near one another and only one puck should be redirected into an offshoot path, it becomes difficult to control a switch so that only one puck is moved into the offshoot path and ensure that the proper puck is pulled from the friction track. This has created the need in many prior art systems to have pucks stop at a gate so that individual pucks can be released and switched one at a time at each decision point on a track.

Another way that singulation has been used in friction track-based systems is to stop the puck at a gate and allow a barcode reader to read a barcode on the sample tube. Because barcode readers are slow relative to the amount of time needed to switch a puck between tracks, scanning introduces hard singulations into the flow on a track and causes all nearby pucks to halt while a switching determination is made. After a determination is made, singulation may be further used to ensure that only the scanned puck proceeds by using a physical blockage to prevent the puck behind the scanned puck from proceeding while the scanned puck is switched.

U.S. Pat. No. 6,202,829 shows an exemplary prior art friction track system that includes actuated mechanical diversion gates that can be used to direct pucks off of the main track onto pullout tracks. As explained therein, the diversion process can require multiple mechanical gates to singulate and separate individual pucks, stopping each puck multiple times and allowing each puck to be rotated so that a barcode can be read before a diversion decision is made. Such a system increases latency and virtually ensures that each time a diversion gate is added to a friction track the gate adds another traffic bottleneck. Such a system results in natural queuing at each diversion gate further increasing the amount of time that each sample spends on the friction track.

While there has been some development of autonomous transport carriers outside the IVD environment, such as industrial and shipping environments, there has yet to be an effective system that uses independently routable and positionable carriers in an IVD setting. One reason for the lack of automated carriers may include the need for precise positioning of vessels in relation to testing stations. For example, a carrier must be able to reliably position itself at a destination to within about a millimeter to allow aspiration of the sample carried. Similarly, the small size needed for carriers in an IVD setting and relatively small size of features of tracks used to transport samples present challenges in adapting systems and techniques used in industrial systems. Accordingly, there is a need for conveying reliable position information to carriers in an IVD setting before semi-autonomous/autonomous transport can be realized in an IVD setting.

SUMMARY

Embodiments of the present invention address and overcome one or more of the above shortcomings and drawbacks by providing devices and systems for providing location information for use by intelligent carriers that transport samples. This technology is particularly well-suited for, but by no means limited to, transport mechanisms in an automation system for use in an in vitro diagnostics (IVD) environment.

Embodiments of the present invention are directed to an automation system having a track with a plurality of track segments having optically encoded marks with pitches and supporting independently movable carriers that can observe the encoded marks. The carriers can be configured to navigate using the marks to determine a current location on the track.

According to one embodiment of the invention, an automation system for use with an automated clinical analyzer includes a at least a first and second track segment, the first and second track segments comprising a first and second set of optically encoded marks, respectively, and a plurality of independently movable carriers configured to observe the first and second sets of optically encoded marks. Furthermore, the first set of optically encoded marks has a first pitch, and the second set of optically encoded marks has a second, finer pitch.

According to another aspect of the invention, the amount of the first pitch is communicated wirelessly to at least one of the plurality of independently movable carriers. According to another aspect of the invention, the amount of the first pitch is encoded in characters in the first set of optically encoded marks. According to another aspect, synchronization information is encoded in characters in the first set of optically encoded marks. According to yet another aspect, an identification of the first track segment is encoded in the first set of optically encoded marks. According to still another aspect, the first set of optically encoded marks is dynamically encoded using an electronic display, which can be an electronic ink display. An additional aspect of the invention is that the first set of optically encoded marks comprises routing information for at least one of the plurality of independently movable carriers. According to another aspect, the plurality of independent carriers is configured to count marks in the first set of optically encoded marks to determine a relative location in the first track segment. In yet another aspect, the first track segment comprises one or more optical landmarks.

According to another embodiment of the invention, an automation system for use with an automated clinical analyzer includes a track comprising at least one track segment comprising at least a first set of optically encoded marks, at least a subset of which are regularly spaced with a first pitch. The automation system also includes at least one movable carrier for transporting a fluid sample and configured to navigate the track using at least the first set of optically encoded marks, including counting the number of optically encoded marks to determine the current location of the movable carrier within the track segment.

According to another aspect of the invention, the amount of the first pitch is communicated wirelessly to the at least one movable carrier. According to another aspect of the invention, the amount of the first pitch is encoded in characters in the first set of optically encoded marks. In another aspect, synchronization information is encoded in characters in the first set of optically encoded marks. In yet another aspect, an identification of the first track segment is encoded in the first set of optically encoded marks.

An additional aspect of the invention is the first set of optically encoded marks is dynamically encoded using an electronic display. The electronic display can include an electronic ink display. According to another aspect, the first set of optically encoded marks comprises routing information for the at least one movable carrier. In another aspect, the first track segment includes one or more optical landmarks. In yet another aspect, the first set of optically encoded marks includes a plurality of rows of marks. In still another aspect, the rows of marks are offset from one another such that observing the first set of optically encoded marks indicates a direction in which the movable carrier is traveling.

According to one embodiment of the invention, a carrier is configurable for use in an automation system in an IVD system and includes a body configured to interface with an automation track and further configured to facilitate carrying a payload. One or more optical sensors are configured to sense optically encoded marks on the automation track. A processor is configured to decode the optically encoded marks and determine at least one of position and velocity of the carrier within the automation system.

According to one aspect of some embodiments, the processor utilizes information about a plurality of pitches in the optically encoded marks to perform the determination. The processor can be configured to receive the information about a plurality of pitches wirelessly or decode the information about a plurality of pitches from characters in the optically encoded marks. According to another aspect of some embodiments, the processor is further configured to determine an identification of a current track section by decoding information from the optically encoded marks. The processor may be further configured to determine the position of the carrier within the automation system by counting at least a subset of the optically encoded marks. According to yet another aspect of some embodiments, the optically encoded marks decoded by the processor can include a plurality of rows of marks.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 4A is a perspective view of an exemplary carrier that can be used with the embodiments disclosed herein;

FIG. 6 is a diagrammatic view of an exemplary routes in an exemplary track configuration that can be used for navigation of sample carriers in certain embodiments;

FIG. 7A is a top view of an exemplary track section for use with embodiments of an encoding scheme;

FIG. 7B is a top view of an exemplary encoding scheme on a track surface, such as that represented in FIG. 7A;

FIGS. 7C-7D are cross-sectional views of exemplary tracks used with embodiments of an encoding scheme;

FIGS. 8A-8D are diagrammatic views of various encoding schemes that can be used in embodiments of the invention;

FIGS. 9A-9D are diagrammatic views of various other encoding schemes that can be used in embodiments of the invention;

FIGS. 11A-11C are diagrammatic views of further encoding schemes that can be used in embodiments of the invention.

DETAILED DESCRIPTION OF ILLUSTRATIVE EMBODIMENTS

Figure 1:
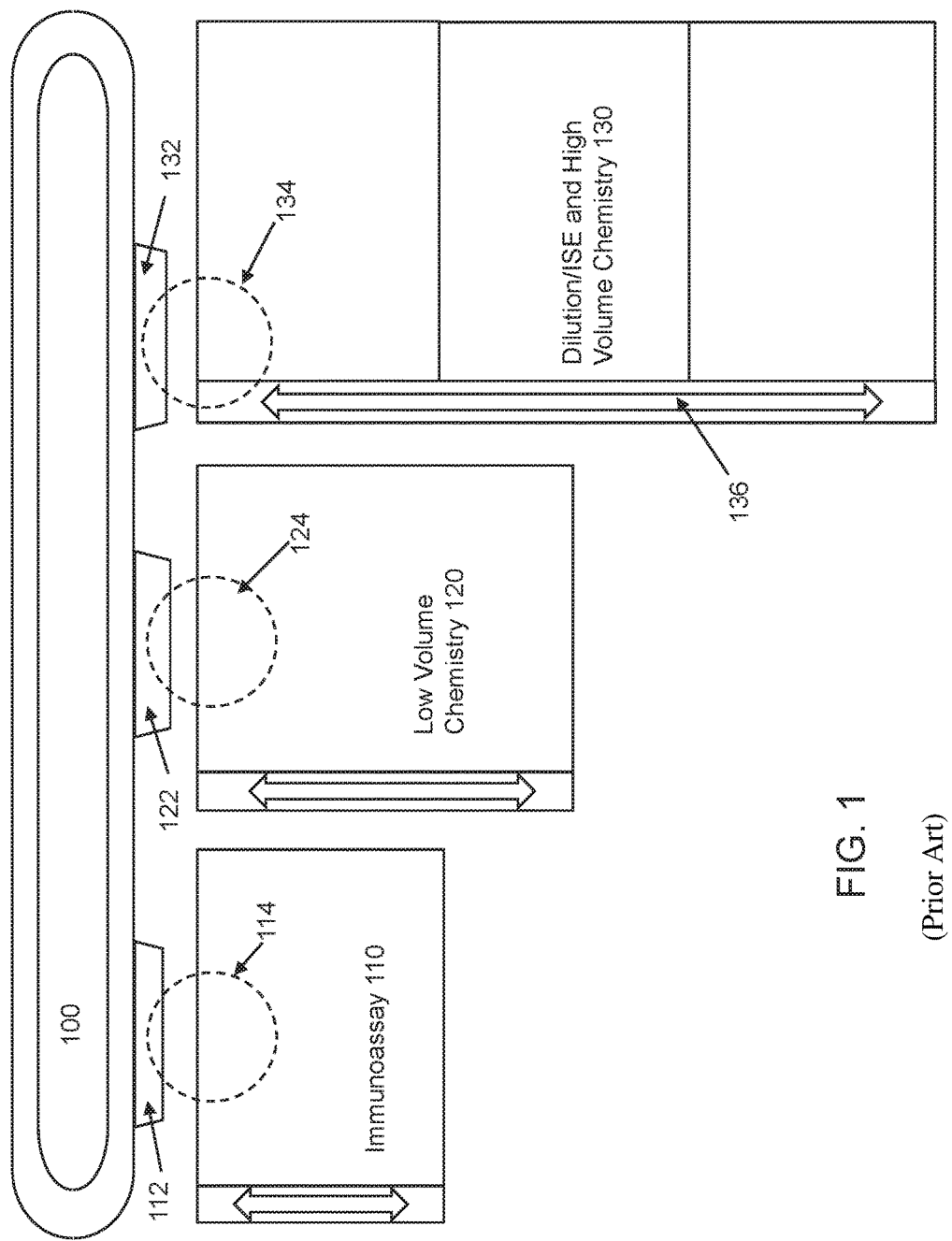
FIG. 1 is a top view of an exemplary clinical analyzer geometry that can be improved by use of the automation system embodiments disclosed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes; maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. WD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each mModule can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

EXEMPLARY EMBODIMENTS

The above problems in the prior art have motivated the discovery of improved apparatus and methods for reliably and/or automatically transporting samples between stations/testing modules within an automated clinical analyzer (analyzer). Specifically, by providing encoded distance or position marks in a track surface, semi-autonomous carriers can be used to reliably transport samples, such as, for example, patient fluid samples in an in vitro diagnostics (IVD) clinical analyzer. These carriers can transport samples substantially faster than prior methods, allowing reliable scheduling of tests, a reduction of traffic in the automation system, and reduced latency and reliable throughput of tests within the analyzer. Some embodiments exploit the semi-autonomy of the sample carriers to provide transit between stations in less than a single operation cycle, effectively removing or greatly reducing automation of sample placement as a performance bottleneck, and allowing more flexible sample scheduling options. The rapid motion can create difficulty in reckoning the position of a carrier with sufficient accuracy in an WD environment. By providing marks in the track surface, a carrier can count marks to provide a robust reference frame for determining position and trajectory information while traversing a linear track in an automation system.

Embodiments of the present invention include systems and methods that provide a more efficient lab automation system to allow samples to be shuttled between and amongst various analyzer testing stations with less latency and more individual control. Embodiments of the present invention can reduce or eliminate queues experienced by samples traversing the automation system. Usually, samples need to undergo many different types of testing in an automated clinical analyzer (analyzer), which may not be available in a single testing station. Testing stations within an analyzer can be adapted for specialized testing. For example, immunoassays may be performed by an immunoassay station that includes certain incubation capabilities and uses specific reagents that are unique to immunoassays. Chemical analysis can be performed by a clinical analyzer and electrolyte chemistry analysis can be conducted by an ion-selective electrode (ISE) clinical analyzer. By using this modular approach, an analyzer can be adapted not only to the types of testing being done on samples, but also the frequency and volume of testing necessary to accommodate the needs of the lab. If additional immunoassay capability is needed, a lab may choose to add additional immunoassay stations and increase overall throughput for immunoassay testing in their system.

An exemplary track geometry, for use in transporting samples within an analyzer typical in prior art configurations, is shown in FIG. 1. This track can include prior art friction tracks, which may introduce problems in designing a track system. However, certain embodiments of the present invention could also use a similar geometry without necessarily employing a friction track for motion. Track 100 can be a generally oval-shaped track that conveys samples in pucks or trays between various stations, such as sample preparation or analyzing/testing stations 110, 120, and 130. Track 100 could be a single direction track or, in some instances, a linear bidirectional track. In this exemplary set-up, each analyzer 110, 120, 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to pullout 112 until analyzer 110 finishes handling a pending sample in sidecar 112 and inserts it back into the main traffic flow of track 100.

In some prior art systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station (or stations) 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system is that the separate friction tracks operate independently and control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm.

Prior art lab automation systems for analyzers generally treat individual analyzer/testing stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

Figure 2A:
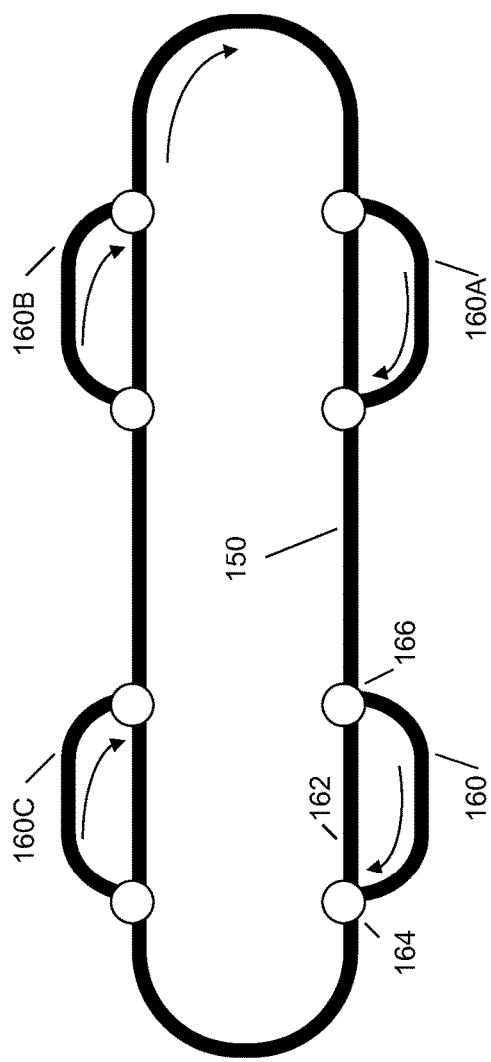
FIGS. 2A and 2B are diagrammatic views of track geometries that can be used with the automation system embodiments disclosed herein.

FIG. 2A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload within the WD environment, such as fluid samples, reagents, or waste. Fluids, such as patient samples, can be placed in a container or vessel, such as a test tube, vial, cuvette, etc. that can be transported by a carrier. Carriers and, by extension, payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample carrier at decision point 166 are described throughout.

Figure 2B:
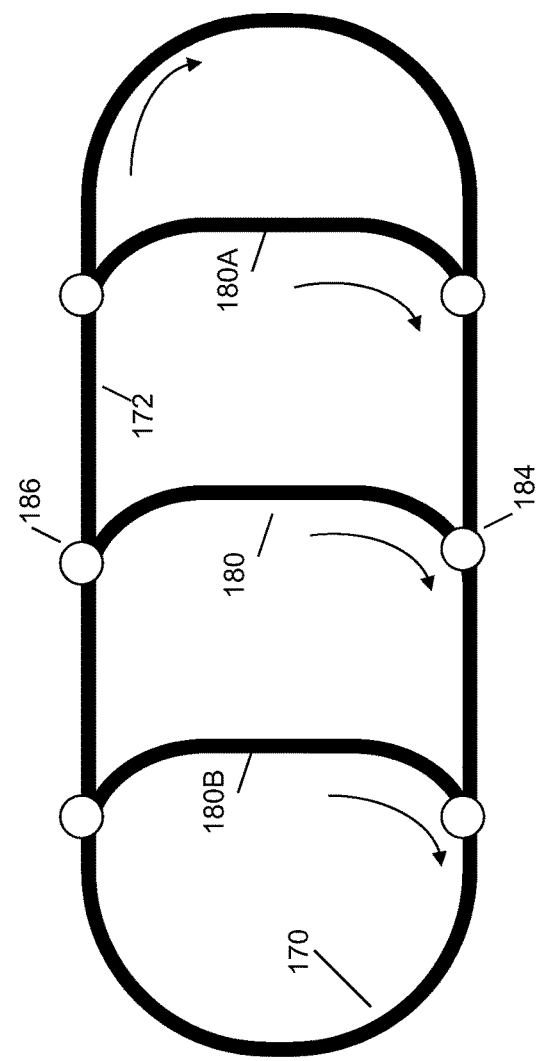

FIG. 2B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path such as path 180. At decision point 186, a sample on the main track 170 can be made to continue on the main track or be diverted onto path 180. Once an analyzer station along handling path 180 is done processing the sample, the sample proceeds to decision point 184 where it may be placed back onto the main path 170.

Figure 3:
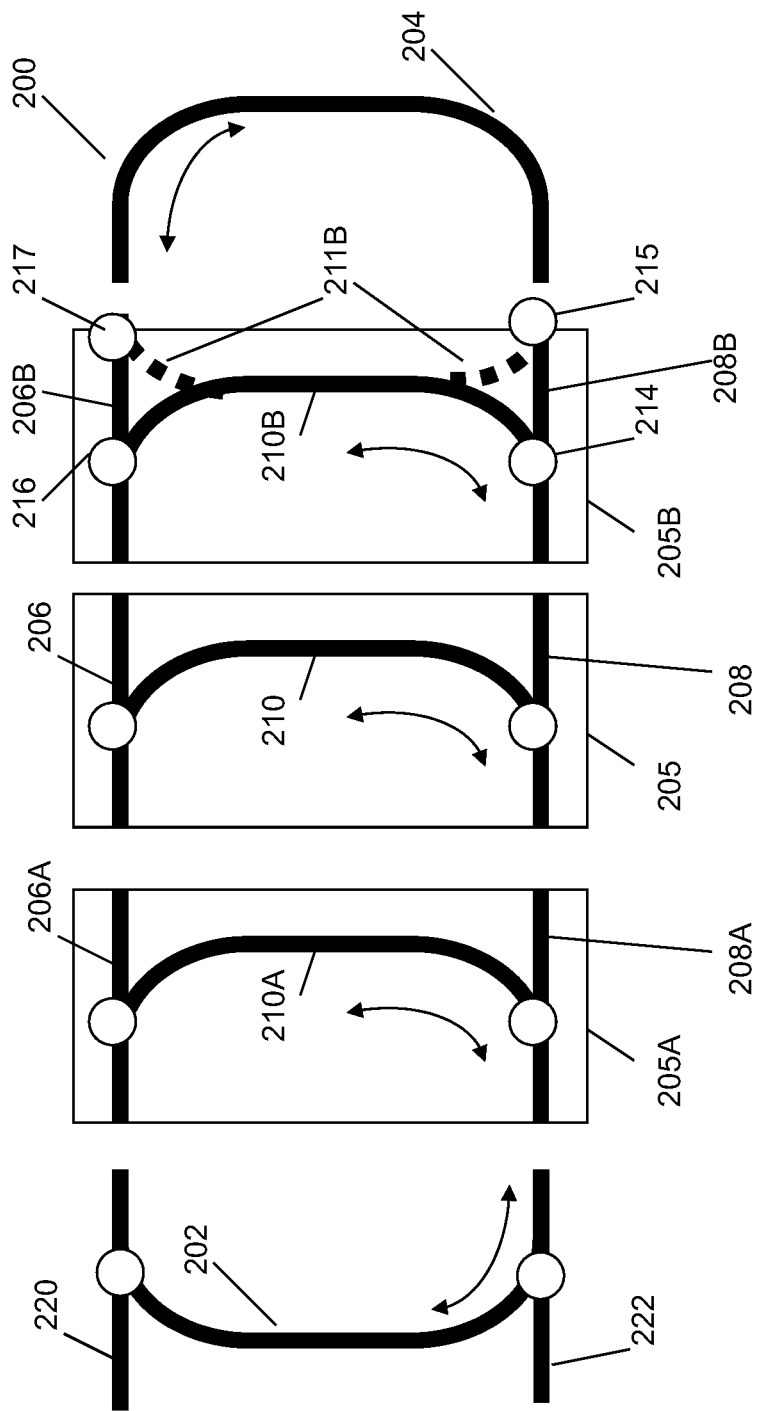
FIG. 3 is a diagrammatic view of an exemplary modular track configuration that can be used with the embodiments disclosed herein.

FIG. 3 shows a modular approach to the automation system track that can be used for certain embodiments of the present invention. In this example, the tracks may be integrated into individual analyzer stations such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems.

With respect to FIG. 3, the track 200 can be broken into modular components that are integrated into analyzer modules. In this exemplary track, modules 205, 205A, and 205B can be combined with one another and optionally other modular track components 202 and 204 to form a track similar to that shown in FIG. 2B. For instance, 205A can be a module that performs the same function as immunoassay 110 (FIG. 1), 205 can be a module that performs the same function as low-volume chemistry module 120 (FIG. 1), and 205B can be a module that performs ISE electrolyte testing, like module 130 (FIG. 1). In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, is that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other RA queues can be eliminated from the modules and the sub-paths (e.g., 210) from the automation system can be used as part of an RA or FIFO queue. That is, if the travel time for a sample between any two points can be bounded to a known time that is similar to that of a carousel (such as predictably less than a portion of an operation cycle), the track 200 can be part of the queue for a given module. For example, rather than using a carousel, module 205 can utilize samples in carriers on sub-path 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module prior knowledge of the arrival time of a sample, each module can prepare resources and interleave tests or portions of tests to more efficiently allot internal resources. In this manner, modules can operate on samples in a just-in-time manner, rather than by using large physical buffers. The effect is that the virtual queue for a given module can be much larger than the physical capacity of the sub-path serving that module, and existing scheduling algorithms can be used. Effectively, each module can treat track 200 as it would treat a sample carousel in a prior art module.

It should be appreciated that by employing virtual queues, in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

If decision points such as 214 and 216 can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and, by extension, the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier, or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing just-in-time access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto carriers on the track 200. When the reagents on track 200 reach the appropriate module, the module can utilize mechanical systems such as an arm or a feeder system that takes the reagents off of the track and places the reagents in the reagents store for the module.

In some embodiments, the individual track portions shown in FIG. 3 and FIG. 2A and FIG. 2B can be operated independently from one another, or can be passive. Independent carrier movement provides advantages over friction-based track systems, such as non-localized conveyor belts where the entire friction track must be moved to effect movement of a sample carrier. This means that other samples also on that track must move at the same rate. This also means that if certain sections operate at different speeds, collisions between passive carriers carrying samples can occur.

FIG. 4A depicts an exemplary carrier 250 for use with the present invention. Carrier 250 can hold different payloads in different embodiments. One payload can be a sample tube 255, which contains a fluid sample 256, such as blood or urine. Other payloads may include racks of tubes or reagent cartridges or any other suitable cartridge. Sample carrier 250 includes a main body 260, which can house the internal electronic components describe herein. The main body 260 supports a bracket 262, which can accept a payload. In some embodiments, this is a shallow hole that is designed to accept a fluid container 255 such as a sample tube, and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Body 260 can include or be coupled to guide portion 266, which allows the carrier 250 to follow a track between decision points. Guide portion 266 can include, for example, a slot to accept one or more rails in the track, providing lateral and/or vertical support. In some embodiments, the guide portion allows the carrier 250 to be guided by walls in the track, such as the walls of a trough-shaped track. The guide portion 266 can also include drive mechanisms, such as friction wheels that allow a motor in the carrier body 260 to drive the carrier or puck 250 forward or backward on the track. The guide portion 266 can include other drive components suitable for use with the embodiments described throughout, such as magnets or induction coils.

Rewritable display 268 can be provided on the top of the carrier 250. This display can include an LCD oriented panel and can be updated in real time by the carrier 250 to display status information about sample 256. By providing the electronically rewritable display on the top of the carrier 250, the status information can be viewed at a glance by an operator. This can allow an operator to quickly determine which sample he/she is looking for when there are multiple carriers 250 in a group. By placing the rewritable display on top of the carrier 250, an operator can determine status information even when multiple carriers 250 are in a drawer or rack.

Figure 4B:
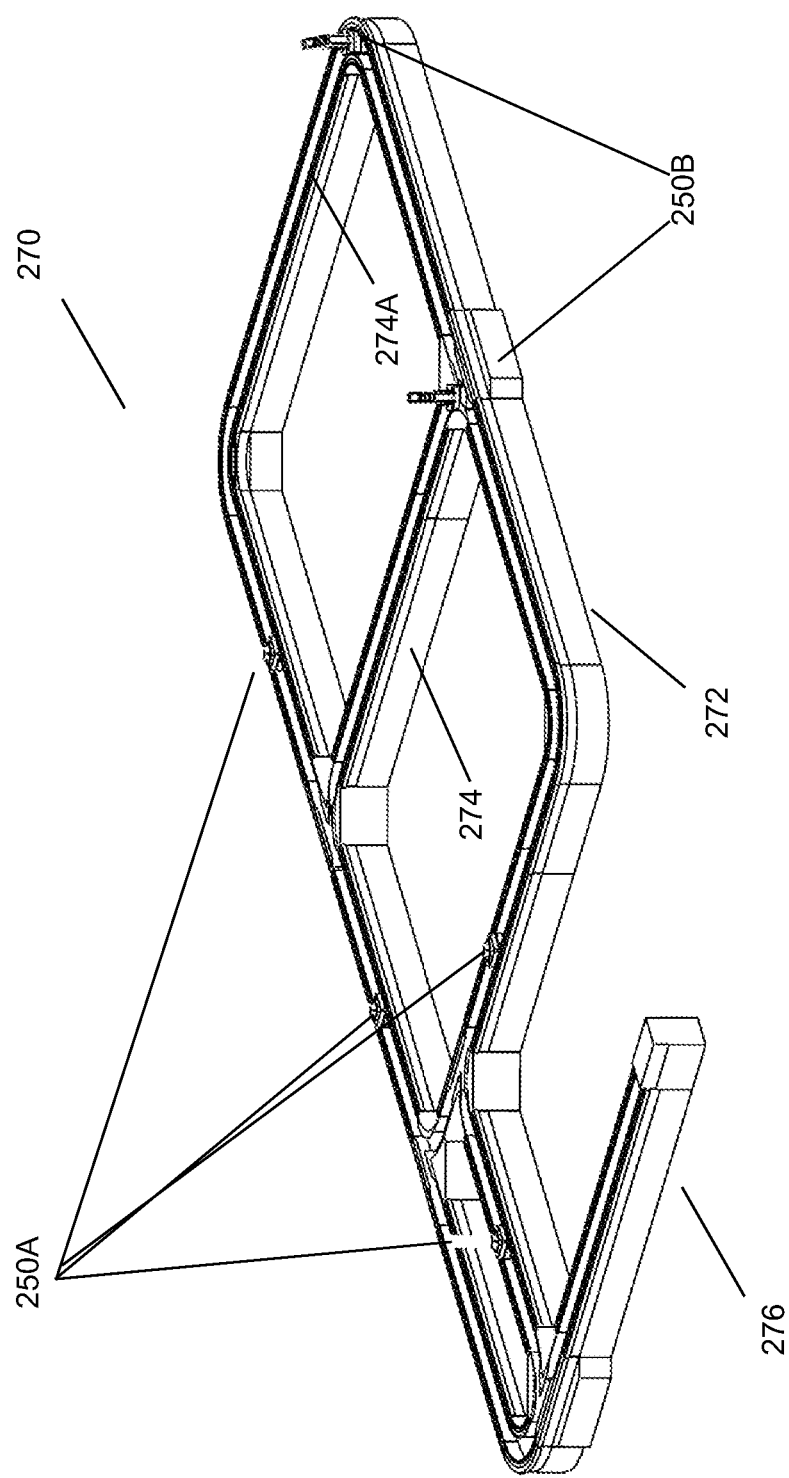
FIG. 4B is a perspective view of an exemplary track configuration that can be used with the embodiments disclosed herein.

FIG. 4B shows an exemplary track configuration 270 for use by carriers 250. In this example, carriers 250A transport sample tubes, while carriers 250B transport racks of tubes along main track 272 and/or subpaths 274 and 274A. Path 276 can be used by an operator to place samples into carriers or remove samples from these carriers.

Figure 4C:
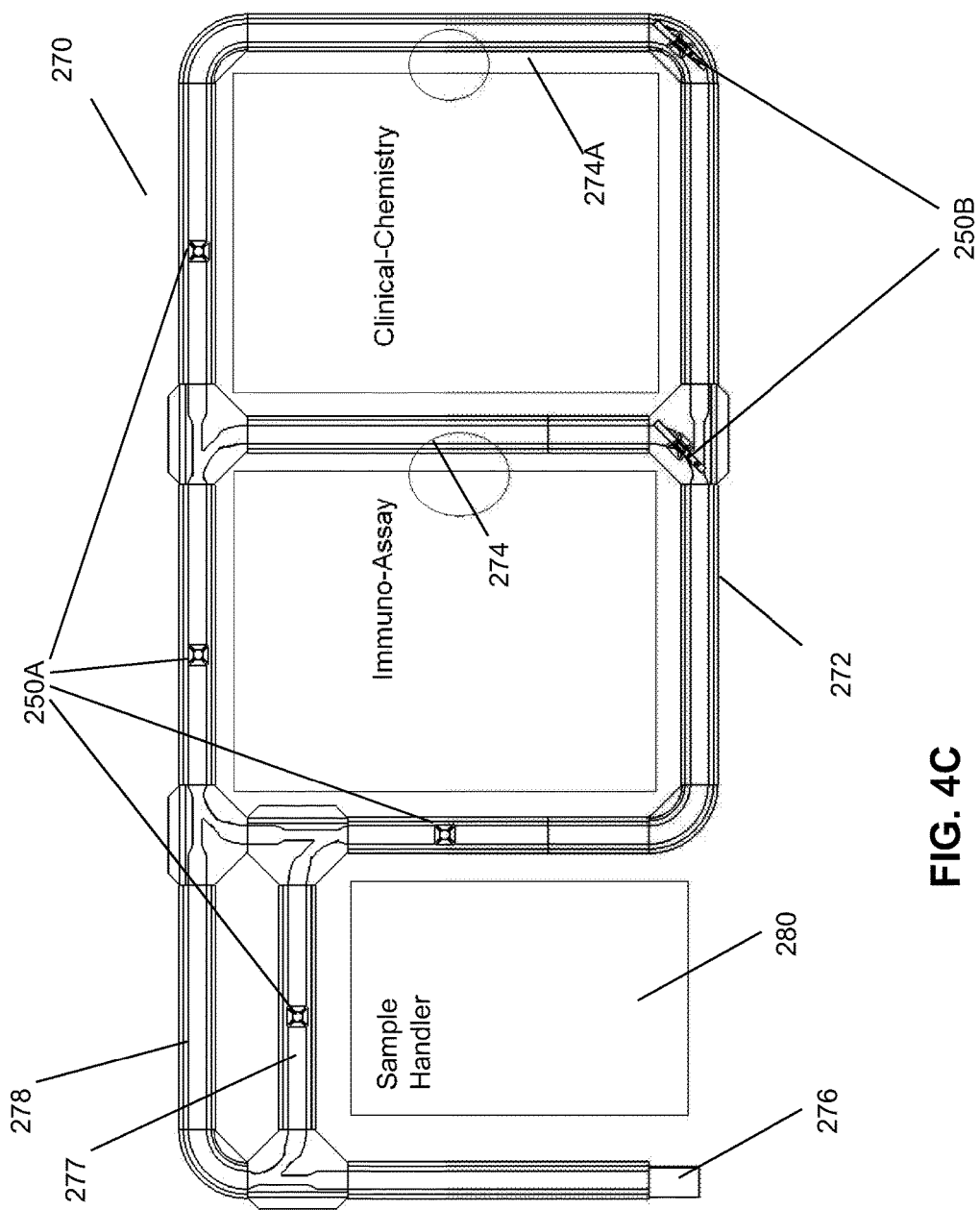
FIG. 4C is a top view of an exemplary automation systems carrier that can be used with the embodiments disclosed herein.

FIG. 4C shows an additional view of an exemplary track configuration 270. In this example, sub-path 274 serves an immunoassay station, while sub-path 274A serves a clinical chemistry station. Input/output lane 276 can be served by a sample handler station 280 that uses sub-paths 277 and 278 to buffer samples for insertion or removal of the samples from the main track 272.

In some embodiments, the sample handler 280 can also load and unload samples or other payloads to/from the carriers 250A and 250B. This allows the number of carriers to be reduced to the amount needed to support payloads that are currently being used by the stations in track system 270, rather than having a vast majority of carriers sitting idle on tracks 277 and 278 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Intelligent Carriers

Whereas prior art lab automation systems utilize passive pucks or trays (e.g., the puck is a simple plastic or rubber brick that lacks active or autonomous systems, power, onboard processing, or control) to reduce cost and complexity, the inventors of the present invention have realized that the added complexity and cost necessary to integrate intelligence and autonomy into individual carriers (which can include intelligent pucks or trays in some embodiments) provides unexpected and important benefits that have been overlooked in traditional lab automation systems. Accordingly, embodiments of the present invention can utilize intelligent independent carriers to enable certain improvements over passive pucks on friction-based tracks. For example, one disadvantage of prior art track systems is that at each decision point the decision for directing a puck is made by the track by rotating the puck and reading a barcode optically. Rotating and optical reading is a relatively slow process. Furthermore, this process can be redundant because the system has knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically.

For example, a carrier can include an onboard optical reader to automatically read a barcode of a payload. The results of the scan can then be stored in the memory of a carrier if the carrier has onboard processing capability. Alternatively, an outside source, such as a hand barcode reader operated by an operator at the time of placing the sample into the carrier, can communicate the barcode information of the payload to the carrier via RF signal or other known means, such as communication protocol using temporary electrical contact or optical communication. In some embodiments, the association of the carrier with the payload can be stored external to the carrier and the identity of the carrier can be conveyed by the carrier to the system by RF, optical, or near field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

By allowing carriers to move independently, carriers can move around the track faster. One key limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For prior-art friction-based track systems, the velocity of the track is typically limited to prevent acceleration and jerk experienced by pucks from exceeding threshold amounts because the entire track moves. However, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section as appropriate, resulting in a substantially higher average speed around the track. This can assist the carrier in traversing the entire track system in less than one machine cycle of the analyzer. These machine cycles can be, for instance 20 or 40 seconds.

Similarly, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near-field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

An autonomous carrier can also include onboard processing and sensor capabilities. This can allow a carrier to determine where it is on the track and where it needs to go, rather than being directed by the track (although, in some embodiments, a central controller sends routing instructions to the carrier to be carried out). For example, position encoding or markers in the track can be read by the carrier to determine a carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position. For example, the carrier may have gyroscopes, accelerometers, or optical sensors that observe speckle patterns as the carrier moves to determine velocity or acceleration, which can be used to extrapolate a relative position.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near-field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths as appropriate. Because each carrier operates independently from one another, a carrier can do this quite quickly without necessarily stopping at each decision point and without waiting for other carriers in a queue. Because these carriers move quickly, there is less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in US Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 5:
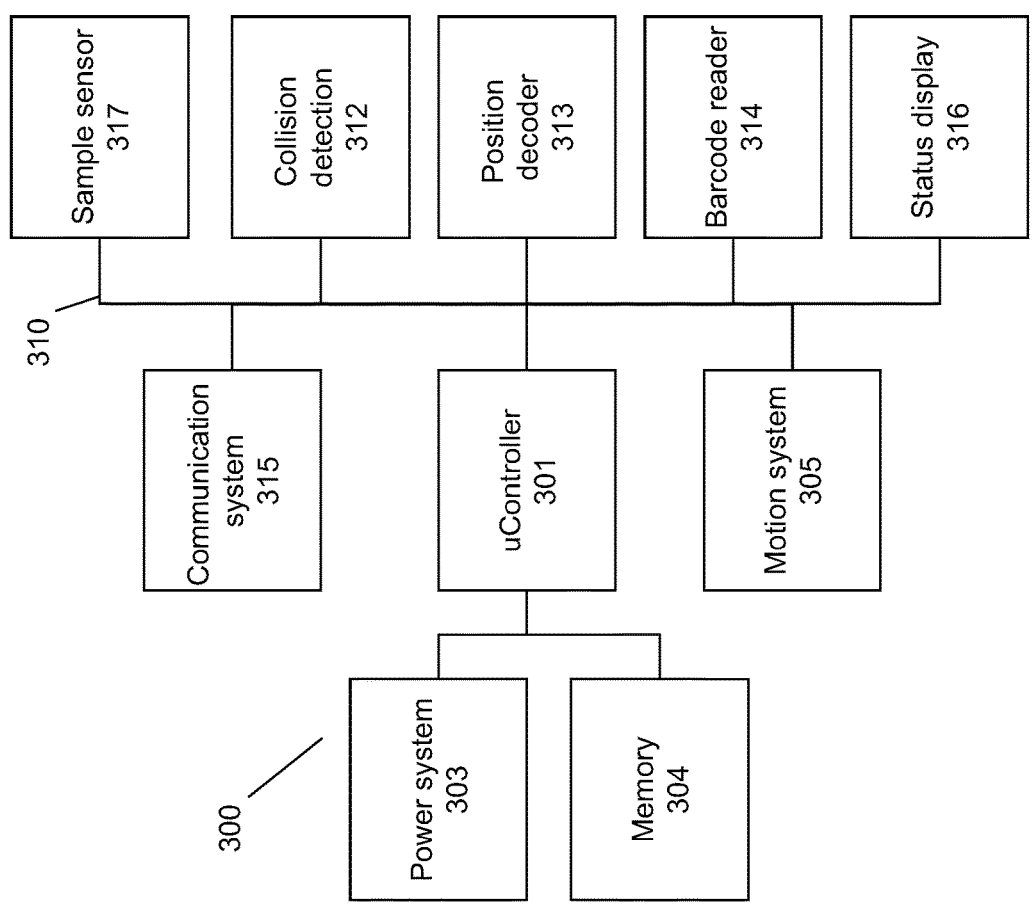
FIG. 5 is a system block diagram of the control systems including onboard active carriers that can be used with certain embodiments disclosed herein.

FIG. 5 shows a top-level system diagram of the control systems and sensors for an exemplary intelligent autonomous carrier 300. Carrier 300 is controlled by a microcontroller 301 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 303 comprises a battery that may be charged as the carrier operates, while in other embodiments, the battery is replaceable or can be manually charged when the carrier is not operating. Power system 303 can include the necessary charging electronics to maintain a battery. In other embodiments, power system 303 comprises a capacitor that may be charged by inductive or electrical contact mechanisms to obtain electrical potential from the track itself, in much the same way a subway car or model train might receive power.

Microcontroller 301 communicates with system memory 304. System memory 304 may include data and instruction memory. Instruction memory in memory 304 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 300, the carrier can keep track of its current status and uses information to intelligently route around the track or convey status information to the track or other carriers.

Microcontroller 301 is responsible for operating the motion system 305, sensors 312, 313, and 314, communication system 315, status display 316, and sample sensor 317. These peripherals can be operated by the microcontroller 301 via a bus 310. Bus 310 can be any standard bus, such as a CAN bus, that is capable of communicating with the plurality of peripherals, or can include individual signal paths to individual peripherals. Peripherals can utilize their own power sources or the common power system 303.

Motion system 305 can include the control logic necessary for operating any of the motion systems described herein. For example, motion system 305 can include motor controllers in embodiments that use driven wheels. In other embodiments, motion system 305 can include the necessary logic to communicate with any active track systems necessary to provide a motive force to the carrier 300. In these embodiments, motion system 305 may be a software component executed by microcontroller 301 and utilizing communication system 315 to communicate with the track. Devices such as motors, actuators, electromagnets, and the like, that are controlled by motion system 305 can be powered by power system 303 in embodiments where these devices are onboard the carrier. External power sources can also provide power in some embodiments, such as embodiments where an LSM provides motive force by energizing coils in the track. In some embodiments, motion system 305 controls devices on or off the carrier to provide motive force. In some embodiments, the motion system 305 works with other controllers, such as controllers in the track, to coordinate motive forces, such as by requesting nearby coils in the track be energized or requesting the movement of local rollers. In these embodiments, motion system 315 can work together with communication system 315 to move the carrier.

Carrier 300 can include one or more sensors. In some embodiments, carrier 300 includes a collision detection system 312. Collision detection system 312 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 300 may be directional, having a front portion and a rear portion. By having a directional geometry, carrier 300 can include a front collision detector and a rear collision detector.

In some embodiments, collision detection information can include information received via the communication system 315. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 300 can also include a position decoder 313. This sensor can extrapolate the carrier's position as described herein. For example, position decoder 313 can include a camera or other optical means to identify landmarks in the track, or observe optical encoding in the track. In some embodiments, position decoder 313 can also include inertial sensors, magnetic sensors, or other sensors sufficient to determine a carrier's current position, direction, velocity, acceleration, and/or jerk.

Carrier 300 can optionally include a barcode reader 314. If equipped with the barcode reader 314, carrier 300 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 304 via communication system 315.

Communication system 315 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 315 can include a transceiver and antenna and logic for operating an RF communication protocol. In some embodiments, communication system 315 can also include near field communication, optical communication or electrical contact components. Information conveyed via the communications system to/from carrier 300 is described throughout this application.

In some embodiments, the carrier can also include a status display module 316. The status display module 316 can include a controller and rewritable electronic display, such as an LCD panel or E-ink display. In some embodiments, the controller is treated as an addressable portion of memory, such that the microcontroller 301 can easily update the status display 316.

In some embodiments, the carrier also includes sample sensor 317. This sensor can be used to indicate the presence or absence of a fluid container in the carrier's tube bracket (which may also be referred to as a tube holder). In some embodiments, this is a momentary mechanical switch that is depressed by the presence of a tube and not depressed when a tube is absent. This information can be used to determine the status of a tube, which can assist in the display of status information by status display module 316.

Routing

The desire for rapid transit times within an analyzer system can make routing difficult. In prior art systems, rapid routing is less critical because samples are generally stopped, singulated, and scanned at each decision point. In those systems, the routing decision for a given decision point can be made while the sample is stopped. Rapid routing decisions are generally desired, and may require determining a switching decision before a sample carrier reaches a decision point. Furthermore, because the carriers move at a rapid rate compared to the prior art, the control of the instantaneous trajectory of a sample carrier can be assisted by real-time processing in order to prevent spilling or damaging IVD samples. In some embodiments, substantially instantaneous trajectory observation and control is conducted onboard each carrier to facilitate real-time control, while the overall routing decisions are made by a central controller that manages a group of carriers. Therefore, in some embodiments of the present invention, the carriers act like semi-autonomous robots that receive global routing instructions from a central controller, but make local motion decisions substantially autonomously.

Because the carriers are actively involved in routing and trajectory control, the carriers should have a way to determine position and velocity information as they traverse the track, for example, of an IVD automation system. While accelerometers can provide acceleration information that can be integrated to determine a relative velocity and position, the precision of this information may be insufficient to be reliable for positioning carriers, and the samples they carry, at certain points in the system. For example, a pipette may need to be accurately placed in a tube on the carrier without contacting the walls of the tube. Therefore, it may be desirable to accurately position a carrier and its payload within about a millimeter at certain points on the track. In other sections of the track, such as straightaways, precise absolute position encoding may not be necessary.

In some embodiments, optical encoding in the track can be used to provide position and/or velocity information to the carrier. Because the need for precision in the positioning information can vary throughout the system, some embodiments use variable pitch encoding to avoid unnecessary encoding precision in parts of the automation system. In some embodiments, the position encoding in some parts of the track system, such as straightaways, can be coarser than the position encoding used in the area surrounding a destination (e.g., a pipetting mechanism).

Using position and/or velocity information obtained through encoding in the track, each carrier can follow routing instructions to reach destinations in the track system quickly, accurately, and without damaging or spilling samples being carried thereon. This position information can be used with information about the topography of the track and physical properties of the carrier's payload to determine the appropriate acceleration and velocity at any moment to minimize lateral forces on curves or allow the carrier to brake with sufficient distance to stop at intended destinations. In addition to position information, the carrier can make trajectory decisions with the assistance of any onboard sensors (such as gyroscopes or accelerometers), or external information received by the carrier (such as information about the position and trajectory of nearby carriers). For example, accelerometers and track encoding information can be used to determine the current velocity, acceleration, and jerk, as well as the current position of a carrier. This information can be used by each carrier to determine its trajectory. In some embodiments, each carrier can convey this information to the system controller or other carriers.

FIG. 6 shows an exemplary routing scenario in automation system 400. Carrier 430 receives routing instructions from central management processor 440 via RF signaling. Carrier 430 can be any suitable embodiment of a carrier, such as carrier 300, shown in FIG. 5. Central management processor 440 can be a microprocessor, software operating on one or more processors, or other conventional computer means suitable for calculating the schedule for multiple carriers within the track system 400. Central management processor 440 can receive position information from multiple carriers, as well as any sensor information from sensors in the track system 400 and/or information reported by the carriers. Central management processor 440 uses the status information of the carriers and track as well as the identity of samples carried by the carriers and the required assays to be performed by the system on these samples.

The exemplary track system 400 shown in FIG. 6 includes a first curve segment A, that connects to straight segment B and a pullout segment G (e.g., a segment that serves a testing station), which serves analyzer/testing station 205A and pipette 420, via decision point 402. Segment B connects to straight segment C and a pullout segment H, which serves analyzer/testing station 205 and pipette 422, via decision point 404. Segment C connects to curved segment D, which serves sample handling station 205C, and pullout segment I, which serves analyzer/testing station 205B and pipette 424, via decision point 406. Segment D connects to straight segment E and the other end of pullout segment I, via decision point 408. That is, there are different paths between decision points 406 and 408—segments D and I, (where segment I is a pullout that can be used to deliver samples to interact with pipette 424). Segment E connects to straight segment F and the other end of pullout segment H, via decision point 410. Segment F connects to curved segment A and the other end of pullout segment G, via decision point 412. In some embodiments, track system 400 includes input and output lanes J and K, which can be used to add or remove carriers at decision points 402 and 412.

In some embodiments, decision points 402-412 are passive forks in the track that carrier 430 can navigate to select a proper destination segment. In other embodiments, decision points 402-412 are active forks that can be controlled by carrier 430 or central management processor 440. In some embodiments, decision points 402-412 are electromagnetically controlled switches that respond to requests by carrier 430, such as via RF or near-field communication. In some embodiments these electromagnetically controlled switches have a default position, such as straight, that the switch will return to once a carrier has been routed. By using default positions for decision points, a carrier may not need to request a position at each decision point, unless it needs to be switched at that decision point.

Scheduler central management processor 440 assigns carrier 430 to a first route, Route 1, to place the carrier 430 and its payload within reach of pipette 420. Carrier 430 is instructed to travel along segment J to decision point 402 and travel onto segment G to stop at a position accessible to pipette 420. In some embodiments, carrier 430 receives the instructions and determines its current location and trajectory to determine a direction and trajectory to use to reach decision point 402. Carrier 430 can also take into account that it will be making a hard right turn at decision point 402 onto segment G. In some embodiments, decision point 402 includes a switching mechanism in the track that can operate under the control of carrier 430. In these embodiments, carrier 430 communicates with the track on approach to decision point 402 to request switching onto segment G. In other embodiments, carrier 430 may have a steering mechanism (such as moveable guide wheel, directional magnets, asymmetric brakes, or the like) that allows carrier 430 to make a right turn onto segment G at decision point 402, without the assistance of an external gate integrated into the track. In these embodiments, carrier 430 engages the steering mechanism at decision point 402 to make the turn onto segment G.

This determination can be based on observing the position encoding in the track, including consulting onboard memory of last known position. Near-field communication from the track can also be used to provide an identification of the current track and encoding scheme being used by the track. Carrier 430 can take into account that it will be making a hard right turn at decision point 402 onto segment G. Using position encoding, carrier 430 can determine where it is in relation to decision point 402 on track J and adjust this trajectory accordingly, to ensure that it approaches the decision point with appropriate velocity.

Carrier 430 can determine its rough location—its current track section, such as section J, by reading encoding in the track, such as optical encoding, or RFID tags. In some embodiments, carrier 430 uses multiple means to determine its location within the track system 400. For example, RFID tags can be used to determine generally on which track segment the carrier 430 is located, while optical encoding or other precise encoding can be used to determine the position within that track segment. This encoding can also be used to determine velocity, acceleration, or jerk by observing changes in the encoding (e.g., derivatives from the position information).

Carrier 430 can use the identification of the current track section to determine the appropriate route to the destination section either by explicit instruction received by the central management processor 440 or by looking up an appropriate route in an onboard database in memory 304, as shown in the onboard control systems in FIG. 5. In some embodiments, the carrier 430 has an understanding of how to reach section G from section J based on a map stored in the memory of carrier 430 in memory 304. This map can include a simple lookup table or a tree of track sections where each node is linked by the corresponding decision points, or vice versa. For example, upon identifying that the carrier is currently in the track section J, the onboard database can inform carrier 430 to proceed to decision point 402 to be switched to the right onto section G.

In the exemplary embodiment shown in FIG. 6, near-field communication (e.g., RFID) can be used to convey the current track section, such as sections A-K, to a carrier 430 when it enters that section by placing RFID tags at the entrance to a track section. Within each section, optical position encoding can be used to convey the relative position of the carrier within that track section. This optical encoding scheme can be, for example, a barcode that includes alternating light and dark lines (e.g., a series of marks) to convey bits of information. In some embodiments, the marks are generally periodically spaced in local sections. The distance between these marks can be referred to as pitch. The pitch is observed as a frequency by the carrier, as the velocity of the carrier creates a periodic signal at any photo-detector observing the marks.

These marks can be applied cost effectively (e.g., relatively inexpensively) to the track by any conventional means including painting or etching the marks into the track surface. These marks may also be active elements, including LEDs regularly spaced on the surface of the track to provide better illumination, and allow some ability to change the encoded pattern dynamically.

In some embodiments, marks are provided by a rewriteable surface, such as a series of E-ink, LCD, or OLED panel displays. This may allow a central controller to update the marks dynamically or as part of a configuration scheme or to convey dynamic content to the carriers, such as individualized routing instructions. For example, a central controller can convey to a first carrier one pitch of encoding marks and another pitch of encoding marks to a second carrier. In this exemplary embodiment, a wider pitch can be used with a carrier that a central controller has deemed capable of higher speed on the track section. By using a wider pitch, a carrier observing the frequency of the marks can be led to believe that it is traveling slower than if the marks being displayed had a finer pitch. A wider pitch can be used for an empty carrier, for example. Meanwhile, a finer pitch can be displayed to a carrier that has a full payload or that a central controller knows will be turning soon. In these embodiments, the position encoding information can be used to convey distance and suggested velocity information to the carrier, or can be used to simply convey velocity information.

Velocity and/or position information can be conveyed via one or more repeating series of alternating lines. These marks can be used by the carrier, much like a clock signal. By knowing the distance between two marks, the carrier can count the marks to determine its relative distance within the track section. The carrier can also determine its velocity within the track section by observing the frequency of these marks or bands. By using binary optical marks, the carrier can read the encoding using simple optical means, such as a photodiode. This can reduce the cost of components of the carrier while still providing reliable position information.

In some embodiments, more than one row of encoding marks can be used. The multiple rows of marks or bands can convey multi-bit information and can convey direction or the pitch of the encoded marks. It will be appreciated that more information can be conveyed using more rows. Multiple rows can be read via a plurality of photo-detectors or a low-resolution camera. The photodetector can also include a lighting source to assist in viewing the marks, like a barcode reader.

In some embodiments, one or more rows of marks can be used and the pitch of these marks can be modulated to convey information, including identification of the track section, direction, absolute distance, or warnings, such as a decision point, such as 402, 404, 406, 408, 410, or 412, or a curve (such as track section D) is approaching. In this manner, each row can be considered an information channel. If a row utilizes an active display that can be actively updated, the row can convey information in a dynamic data channel that is tailored to the carrier receiving it.

In some embodiments, marks may not be entirely binary (e.g., black-and-white). For example, in some embodiments, the size of the mark varies along the track. The size of the mark can be used to convey information, such as making certain marks more prominent and using these marks for synchronization. By using synchronization marks, the encoding scheme can ensure that carriers do not miscount the position marks. For example, a larger mark may be used every 20 marks and can be used like a checksum bit for a carrier to rectify its position count.

In other embodiments, marks can be of multiple colors. The color of marks can convey certain information, such as the pitch of the encoding or the current track section. For example, black-and-white marks may be used in areas where high precision is needed, such as around pipettes, while red and white marks may be used on track sections that are near decision points or curves to indicate to a carrier that it should slow down. That is, the color can act as a warning. Similarly, encoding after obstacles such as decision points may be colored green to convey to carriers that it is an appropriate area to accelerate. In other embodiments, black-and-white marks may be of a certain known pitch while red and white marks are of a rougher pitch. Marks can also be reflective or made to absorb light on an otherwise reflective surface.

In addition to black and white marks (or any other contrasting color combination) a track system 400 can convey position information via other artifacts. For example, the track can include landmarks, such as LEDs, or optical symbols that stand out from normal barcode-like marks.

Landmarks can indicate important features in the track, such as a stopping point for a test station, a braking zone entering a curve, or a braking zone approaching a decision point.

In some embodiments, there are two types of landmarks. A first landmark may include the destination of the carrier. The carrier can determine if it is nearing its destination based on track encoding or a landmark feature, such as an LED, and use this information to begin stopping or complete a stopping procedure. For example, a carrier may be instructed to stop at a precise location accessible to a pipette. This precise location may include an LED in the wall or floor of the track to assist a carrier in the stopping at a precise location with millimeter accuracy. In some embodiments, a carrier calculates a trajectory to get it in a rough location of its destination, while precise encoding near the destination LED can provide finer precision near a reference point. At the destination, the local encoding can be precise with a fine pitch to accurately position a carrier relative to a reference point, such as the start of a track section or a landmark indicating the center of the pipette accessible area.

Another available landmark could indicate a decision point. Using warning LEDs or marks in the encoding in the track can convey the position of an upcoming decision point to a carrier relative to the carrier's current location. LEDs can provide dynamic encoded information. For example, a central scheduler may illuminate an LED at a braking position on the track some distance before a decision point. This can alert the carrier to decelerate to prevent unnecessary acceleration or collision. In some embodiments, if the carrier is not scheduled to turn at a decision point, the central scheduler can refrain from illuminating an LED. A carrier that does not need the landmark can simply ignore the landmark. Braking landmarks can serve as a failsafe to rectify a carrier's trajectory before turning. If the carrier will be turning and it observes a landmark that it did not expect, it can indicate that the extrapolated location perceived by the carrier is false. It may be necessary to update the trajectory to begin decelerating so that the velocity of the carrier is slow enough when it turns at the decision point to prevent unnecessary lateral forces that could harm or spill a sample.

FIG. 7A illustrates different positions at which a carrier 430 can stop. In this example, pipette 420 operates a small sample queue. Here, carrier 430A stops before pipette 420 at position A. Meanwhile, carrier 430B stops at position B directly under pipette 420. This allows pipette 420 to interact with the sample carried by carrier 430B. Carrier 430B may be required to stop within a precise location with respect to position B to allow pipette 420 to accurately interact with the sample. For example, a precise location may include locating carrier 430B within a millimeter of position B. In other embodiments, more precise positioning may be provided. For example, in one embodiment within 0.5 mm; for example, in another embodiment within 0.1 mm. If the local queue is random access, another carrier 430C may be positioned at position C while it waits to interact with pipette 420 at position A or B. The exemplary station shown in FIG. 7A may include testing station 205A (see FIG. 6), but similar examples may exist at the stations served by pipettes 422 and 424.

To achieve precise position encoding around pipette 420, the marks shown in FIG. 7B may be used. Marks 500 can be placed or attached onto the left side wall 460, the right side wall 450, or the bottom surface 470 (see FIG. 7A). In this exemplary embodiment, encoding 500 includes two parallel rows of regularly repeating marks 510 and 530. In this example, marks 510 and 530 share the same pitch, but are phased shifted relative to one another. When shifted asymmetrically, as shown in FIG. 7B, the marks can convey direction. Observing both row 510 and row 530 will indicate the direction the carriers traveling. For example, when the carrier is traveling backwards (towards the top of the figure), the marks in row 530 will appear to precede those in row 510. When the carrier is traveling forward (towards the bottom of the figure), the marks in row 510 will appear to be ahead of those in row 530. The orientation of the encoding in FIG. 7B is arbitrary for illustration. For example, if etched on a vertical surface, row 510 may be a bottom row, while row 530 is a top row.

In some embodiments, only a single row need be used to give both position and direction. If the carrier is equipped with two adjacent photodetectors spaced relative to one another at a distance that is not a multiple of the picture the marks (such as spaced closer than adjacent marks), observing pulses in both photodetectors will reveal the direction the carrier is traveling. For example, when traveling forward, the fore photodetector will observe a mark before the aft photodetector. In some embodiments, a laser is used to illuminate the encoding resulting in a speckled pattern, like that observed in an optical mouse. This allows the carrier to determine direction and velocity information easily with a single row of position encoding.

In some embodiments, an LED 505 can illuminate at a predetermined position, such as position B (FIG. 7A), to indicate the ideal location for stopping to interact with pipette 420. In some embodiments, pipette 420 can move to multiple positions, including positions A and C. In these embodiments, additional LEDs can be placed at those locations and illuminate when a carrier is required to stop at those positions. If the carrier is not supposed to stop at a position, the LED can optionally be turned off (or not illuminated), so that the carrier will not see the landmark.

FIGS. 7C and 7D show cross-sections of exemplary tracks 400 that can be used with the present invention. These cross-sections have multiple surfaces that can be used for encoding position information. For example, FIG. 7C shows a trough-like track having a bottom surface 472, a right surface 452, a left surface 462, and at least one top surface 482 also having a top and bottom surface. Any of these surfaces may be chosen for encoding information. A suitable carrier that travels on this track can then include photodetectors or other optical detectors positioned to observe the marks. The track in FIG. 7D is a monorail-type structure. This track has right and left bottom surfaces 475 and 474, respectively, right and left vertical faces 454 and 464, respectively, and at least one top surface 484. Similarly, any of these surfaces can be chosen as appropriate for encoding information.

Figure 8C:
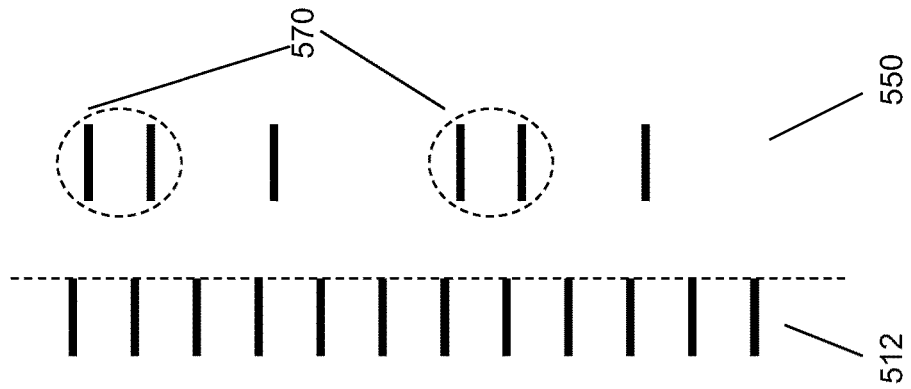
Figure 8B:
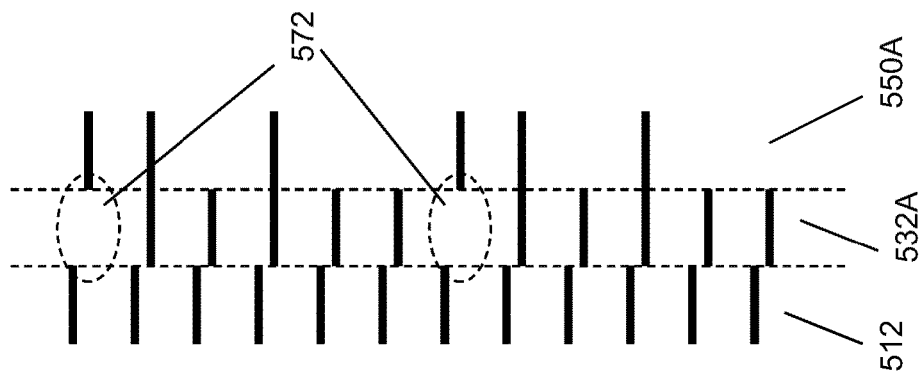
Figure 8A:
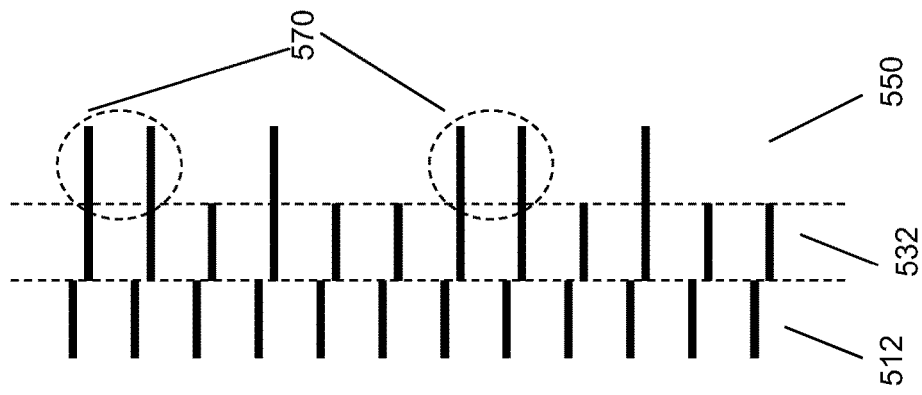

FIGS. 8A-8C show alternate embodiments for encoding additional information in the position encoding. In the example shown in FIG. 8A, there are three rows/channels of encoded information. Rows 512 and 532 include regularly spaced marks that reveal position and direction information. As explained above, a single row can be substituted for these two rows if the carrier has suitably configured photodetectors. Row 550 includes irregularly spaced marks, which can be periodically repeated. These irregularly spaced marks can be called characters. The characters in row 550 can be used to convey information such as the track encoding pitch, the current track section, absolute position information, or any other suitable information. Because row 550 is used with regularly spaced rows 512 and 532, the information in row 550 can be used for coarse absolute positioning information or other data while rows 512 and/or 532 can be used for accurate local positioning based on counting.

In this example, row 550 has synchronization information in marks 570. In this example, two closely spaced marks can be a special character used to synchronize data or synchronize positioning counts as explained throughout.

FIG. 8B shows an alternate encoding. Here, position or data frame synchronization characters 572 can be placed in row 532A. The carrier can observe the gaps in the otherwise regularly spaced pattern and use this information to synchronize with the track encoding. Meanwhile row 550A can be more efficient as a data channel unburdened by frame synchronization characters.

FIG. 8C shows yet another embodiment of position and data encoding. In this embodiment, only one regularly spaced row 512 is used. Meanwhile, data channel 550 can be used for pitch, rough absolute position encoding, or other data. In this embodiment, the carrier may determine its direction via, for example, an accelerometer observing the direction of travel of the carrier using more than one photodetector, or other suitable means. In the embodiment shown in FIG. 8C, the left-hand marks 512 may act as a clock signal for data in row 550. It will be appreciated by one of ordinary skill in the art that any known encoding scheme used for electrical signals may also be adaptable for use in these encoding schemes. For example, a two row encoding scheme, such as that represented in FIG. 8C, could use an encoding scheme similar to a visual version of an I2C bus.

In some embodiments, the marks can be changed dynamically, such as including at least one row of marks 550 that includes LCD or E-ink displays to send information optically to the carrier. In these embodiments, it may not be necessary for a central controller to communicate wirelessly with a carrier because row 550 could act as a low bandwidth data channel to convey dynamic information to a carrier. For example, data row 550 can be used to convey updated routing information to a carrier as it traverses the track. In some embodiments, there can be multiple channels of data 550.

It should be noted that the cost to add information in the encoding on the track can be relatively low, particularly where no dynamic information is encoded, because those encoding channels/rows can be painted or etched. The only substantial costs associated with adding multiple rows may be caused by the increased cost of the hardware used by a carrier in a multiple rows or channels configuration. It should also be noted that all rows do not need to share a single surface, as multiple surfaces may be available as illustrated in FIGS. 7C and 7D.

FIG. 8D illustrates an embodiment in which the data channel 554 can be used to identify the local pitch of regularly spaced rows 514 and 534, or other local information. In this example, synchronization character 570 can be used to determine that data character 580 is two positions away, indicating a first pitch. Subsequent frame synchronization character 570A can be used to determine that data character 582 is one position away. This can indicate a second pitch, which in this example is a wider pitch. It should be noted that any of the other frame synchronization techniques described can be used. Similarly, some embodiments may include only a single regularly pitched encoding channel.

FIGS. 9A-9D show encoding schemes in which the rows of pitched marks can be used to encode synchronization marks or even data. For example, FIG. 9A illustrates two regularly pitched rows 516 and 536, where the absence of the mark in row 536 acts as a synchronization character 576. In FIG. 9B, regularly pitched channels 517 and 537 include synchronization and data. The absence of two marks at position 577 can indicate a synchronization of a position count, as well as a single bit of data (or fraction thereof in embodiments where error coding is used). This data can be used to identify the pitch, track ID, etc. As shown in FIG. 9C, the left-hand row 518 can have an absent character 578 to indicate synchronization information while the right-hand row 538 includes regularly pitched marks. As shown in FIG. 9D, a single row of marks 518A can also be used to include both synchronization marks 578A, as well as position marks at otherwise regular intervals. In these embodiments, the carrier can use the techniques described herein to determine direction without requiring a second encoded row. In some embodiments, missing marks 578A can also be used to convey low-bandwidth data. For example, the presence or absence of every $10^{th}$ mark can convey data, such as track pitch or track section ID.

Figure 10:
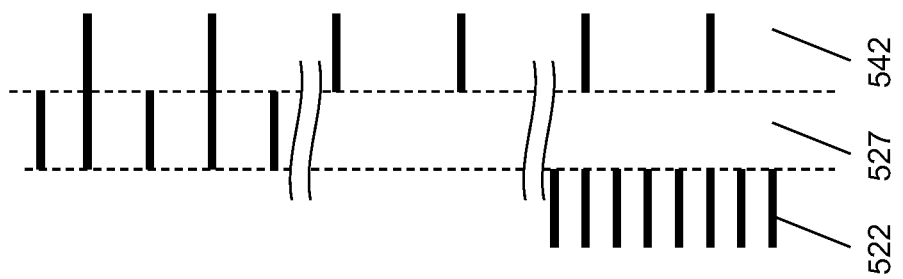
FIG. 10 is a diagrammatic view of an encoding scheme having multiple rows of marks with different pitches that can be used in embodiments of the invention.

FIG. 10 shows an alternate embodiment, whereby multiple pitches can be used in multiple rows. In some embodiments, several pitches can be used in multiple rows 522, 527, and 542. In some embodiments, this pitch information can be encoded throughout the entire track. In the embodiment shown in FIG. 10, coarse pitch information 542 is encoded throughout, while medium pitch information 527 is encoded at certain portions of the track, such as near decision points. Meanwhile, fine pitch information 522 is encoded at locations that are particularly sensitive to accuracy in positioning, such as around destinations (e.g., a pipette station).

Figure 11B:
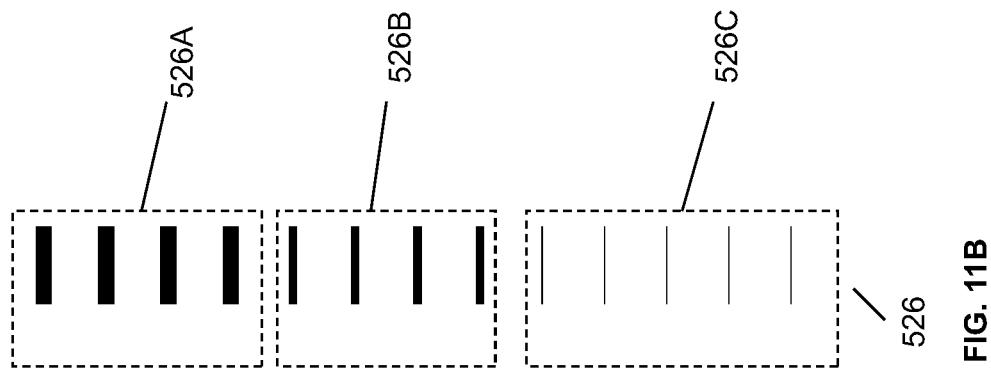
Figure 11A:
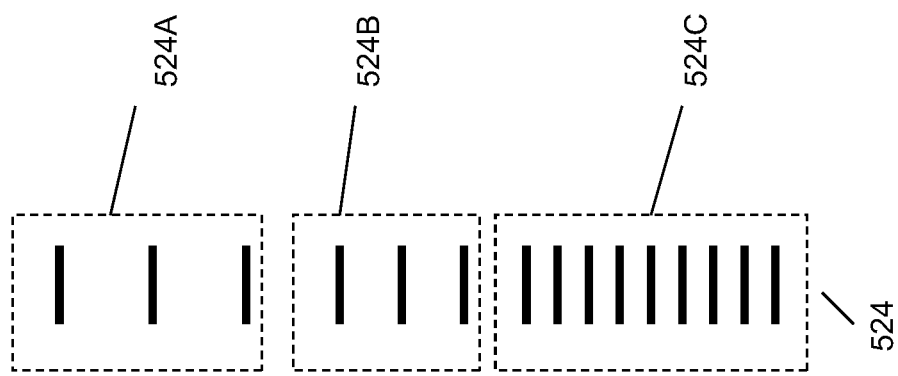

FIG. 11A shows an embodiment in which a variable pitch encoding can be used without an optical indicator of pitch. In this embodiment, encoded row 524 includes multiple sections of regularly spaced marks 524A, 524B, and 524C, which are all encoded with different pitches. Pitch information can be conveyed through near field communication to a receiver in the carrier. In some embodiments, no pitch information is conveyed to the carrier. Instead, the pitch is chosen based on the conditions of the track, such as a straightaway or curve. This can convey the predetermined ideal maximum speed through a section of the track based on curvature or conditions. Wider pitch 524A may be used on a faster section of track (e.g., a straight away), medium pitch 524B may be used on slower sections (e.g., a curve), while finer pitch 524C can be used at destinations (e.g., a work station). A carrier observing the frequency of the marks relative to its own internal clock will see the same frequency in section 524A and section 524C if an appropriate faster speed is used in 524A and an appropriate slower speed is used in 524C.

These variable pitch marks can still be used for distance acquisition. Each carrier can have an internal reference for the "distance" of a track section listed not by physical distance, but by marks on the track. For example, a short track section with fine pitch, such as near a pipette, can have a large distance when measured in marks, such as 500 (e.g., a 50 cm section with 1 mm pitch). Meanwhile, a longer section of high speed track, such as a straight away, can have a few number of marks with a low pitch count, such as 15 (e.g., a 150 cm track section with a pitch of 10 cm). In some embodiments, the pitch can be chosen to act as a speed throttle for the carriers, which can make trajectory decisions easy and reduce computation requirements to reduce the cost of producing carriers.

FIG. 11B shows an embodiment in which a single row of marks 526 is encoded with regularly spaced marks, but marks are different widths. This can allow a single row of optical encoding positioning information to convey both a clock signal in the pitch, as well as other information/data in the observed pulse width. For example, section 526A may convey a faster speed section of track, 526B may convey a medium speed section of track, while section 526C may convey a slow speed section of track. In some embodiments, the width of a mark can also be used to convey the current pitch being used. The width of the marks can be called a duty cycle or pulse width of the marks, as the perceived relative time a sensor detects light or dark areas will change based on the width even though the frequency/pitch does not change. The marks can thereby be used to convey information via a pulse width module.

FIG. 11C shows an embodiment similar to that shown in FIG. 11B. In this embodiment, encoded row 528 encodes a data channel with the bit rate substantially near the pitch of the encoding. (It should be noted that error coding schemes can also be used such that each apparent bit is a fraction of a bit, allowing for larger hamming distances in the signal.) In this embodiment, a special synchronization character 579 can include two regularly spaced marks that overlap, while all other marks are regularly spaced but have varying widths to convey data. In this regard, the embodiment shown in row 528 is much like a continuous barcode. Synchronization mark 579 may be regularly placed throughout the encoded track and act to synchronize data frames.

It will be appreciated that any suitable encoding scheme can be used to convey data along with positioning information. For example, regularly spaced marks can have a width that is chosen based on a Manchester-based encoding. Manchester encoding allows both synchronization information in regularly spaced marks as well as data in the character of those marks. It will be appreciated that many encoding schemes used in the wireless space that encode both data and clock information in a single signal can be used in the optical encoding scheme of the present invention. This can allow static or dynamic (if marks are rewritable) delivery of data as well as precise positioning based on the pitch of the marks.

It should also be appreciated that the precision with which carriers determine their position can be greater (or less) than the pitch of the marks. For example, sub-pitch position accuracy may be achievable by using two analog (or at least multi-state) photodetectors spaced closely apart. When these two photodetectors observe the same mark, the precise location of the carrier relative to that mark can be determined by comparing the relative intensity of the mark observed by both the photodetectors. For example, if two photodetectors are positioned to partially observe the same mark, the photodetector with the stronger signal is determined to be proportionally closer to the mark. This relative observation can be used to achieve sub-millimeter accuracy even when the pitch of the marks encoded in the track is greater than a millimeter.

It will be appreciated that any of the encoding schemes shown in FIGS. 11A-11C can be encoded dynamically with an active display, such as an LCD or E-ink display. In some embodiments, the marks used by any of these encoding schemes can include illuminated surfaces such as LEDs to create the marks or spaces between marks to increase the readability of the encoding. These LEDs can also be dynamic.

In embodiments where a carrier has some steering capability and can turn at a decision point without the assistance of the next internal switch, the carrier can engage its steering mechanism to direct it to the appropriate path upon approaching the decision point. After turning at the decision point (or proceeding without turning) a carrier returns to step 504 to determine its next trajectory.

Embodiments of the present invention may be integrated with existing analyzers and automation systems. It should be appreciated that carriers may be configured in many shapes and sizes, including layouts and physical configurations suitable for use with any contemplated analyzer or instrument. For example, in some embodiments, a carrier may include multiple slots for carrying multiple samples around an automation track. One embodiment, for example, may include a physical layout of a tube-holding portion of a carrier with multiple slots in one or more transport racks. Each rack may include multiple slots (e.g., five or more slots), each slot configured to hold a tube (e.g., a sample tube).

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. An automation system configured for use with an automated clinical analyzer comprising:
    a track comprising at least a first and a second track segment, the first and second track segments comprising a first and second set of optically encoded marks, respectively; and
    a plurality of independently movable carriers comprising a receptacle for accepting a sample fluid tube and at least one optical sensor configured to optically observe the first and second sets of optically encoded marks,
    wherein the first set of optically encoded marks comprises a first set of periodic marks having a first pitch defined by a repeating distance between the periodic marks in a direction of travel of the plurality of independently movable carriers, and the second set of optically encoded marks comprises a second set of periodic marks having a second, finer pitch that is finer than the first pitch in the direction of travel,
    wherein each of the plurality of independently movable carriers is further configured to adjust a velocity in response to observing each of the first and second pitches,
    wherein the first and second set of optically encoded marks each have a horizontal and vertical dimension, and each of the first and second set of optically encoded marks is larger in the horizontal dimension than the vertical, and
    wherein the at least one optical sensor is configured to observe the first and second set of optically encoded marks when the horizontal dimension of each of the first and second set of optically encoded marks is substantially perpendicular to the direction of travel of the plurality of independent carriers.

2. The automation system of claim 1, further comprising a central controller, wherein the amount of the first pitch is communicated wirelessly from the central controller to at least one of the plurality of independently movable carriers.

3. The automation system of claim 1, wherein the first set of optically encoded marks further comprises characters that encode an amount of the first pitch.

4. The automation system of claim 1, wherein the first set of optically encoded marks further comprise at least one synchronization mark that is encoded in characters in the first set of optically encoded marks.

5. The automation system of claim 1, wherein the first set of optically encoded marks further comprise an identification of the first track segment that is encoded in the first set of optically encoded marks.

6. The automation system of claim 1, wherein the plurality of independent carriers are configured to count marks in the first set of optically encoded marks to determine a relative location in the first track segment.

7. The automation system of claim 1, wherein the first track segment comprises one or more optical landmarks.

8. An automation system configured for use with an automated clinical analyzer comprising:
   a track comprising at least one track segment comprising at least a first set of optically encoded marks; and
   at least one movable carrier comprising a receptacle configured to accept and for transporting a fluid sample tube and at least one optical sensor configured to optically detect at least a first set of optically encoded marks and configured to navigate the track using at least the first set of optically encoded marks, including counting the number of optically encoded marks to determine the current location of the movable carrier within the track segment,
   wherein at least a subset of the first set of optically encoded marks are periodically spaced with a first pitch defined by a repeating distance between the periodically spaced marks, in a direction of travel of the at least one movable carrier,
   wherein the first set of optically encoded marks each have a horizontal and vertical dimension, and each of the first set of optically encoded marks is larger in the horizontal dimension than the vertical, and
   wherein the at least one optical sensor is configured to detect the first set of optically encoded marks when the horizontal dimension of each of the first set of optically encoded marks is substantially perpendicular to the direction of travel of the plurality of independent carriers.

9. The automation system of claim 8, further comprising a central controller, wherein the amount of the first pitch is communicated wirelessly from the central controller to the at least one movable carrier.

10. The automation system of claim 8, wherein the first set of optically encoded marks further comprises characters that encode an amount of the first pitch.

11. The automation system of claim 8, wherein the first set of optically encoded marks further comprise synchronization information that is encoded in characters in the first set of optically encoded marks.

12. The automation system of claim 8, wherein the first set of optically encoded marks further comprise an identification of the first track segment that is encoded in the first set of optically encoded marks.

13. The automation system of claim 8, wherein the first track segment comprises one or more optical landmarks.

14. The automation system of claim 8, wherein the first set of optically encoded marks comprise a plurality of rows of marks.

15. The automation system of claim 14, wherein the rows of marks are asymmetrically offset from one another such that observing the first set of optically encoded marks indicates a direction in which the movable carrier is traveling.

16. A carrier configured for use in an automation system in an IVD system, comprising:
   a body configured to interface with an automation track and comprising a receptacle for accepting a sample fluid tube;
   one or more optical sensors configured to sense optically encoded marks on the automation track;
   a processor configured to decode the optically encoded marks and determine at least one of a longitudinal position and velocity of the carrier within the automation system by at least one of counting the number of the optically encoded marks that the carrier has passed and observing a frequency of the optically encoded marks as the carrier moves, wherein the optically encoded marks comprise at least one set of periodic marks that have a regular pitch, defined by a repeating distance between the periodic marks, in a direction of travel of the carrier,
   wherein the optically encoded marks each have a horizontal and vertical dimension, and each of the optically encoded marks is larger in the horizontal dimension than the vertical, and
   wherein the one or more optical sensors is configured to sense each of the optically encoded marks when the horizontal dimension of each of the optically encoded marks is substantially perpendicular to the direction of travel of the plurality of independent carriers on the automation track.

17. The carrier of claim 16, wherein the processor utilizes information about a plurality of pitches in the optically encoded marks to perform the determination.

18. The carrier of claim 17, wherein the processor is configured to wirelessly receive the information about a plurality of pitches.

19. The carrier of claim 17, wherein the processor is configured to decode the information about a plurality of pitches from characters in the optically encoded marks.

20. The carrier of claim 16, wherein the processor is further configured to determine an identification of a current track section by decoding information from the optically encoded marks.

21. The carrier of claim 16, wherein the processor is further configured to determine the position of the carrier within the automation system by counting at least a subset of the optically encoded marks.

22. The carrier of claim 16, wherein the optically encoded marks decoded by the processor comprise a plurality of rows of marks.

* * * * *